US012599869B2

(12) United States Patent (10) Patent No.: US 12,599,869 B2

Noguchi (45) Date of Patent: Apr. 14, 2026

(54) GAS SEPARATION METHOD AND GAS SEPARATION APPARATUS

(71) Applicant: Mitsubishi Chemical Corporation, Tokyo (JP)

(72) Inventor: Naoki Noguchi, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 336 days.

(21) Appl. No.: 18/308,352

(22) Filed: Apr. 27, 2023

(65) Prior Publication Data

US 2023/0264142 A1 Aug. 24, 2023

Related U.S. Application Data

(63) Continuation of application No. PCT/JP2021/039318, filed on Oct. 25, 2021.

(30) Foreign Application Priority Data

Oct. 29, 2020 (JP) ................................. 2020-181559

(51) Int. Cl.
  B01D 53/02 (2006.01)
  B01D 53/22 (2006.01)
  (Continued)

(52) U.S. Cl.
  CPC ............. B01D 53/22 (2013.01); B01D 53/30 (2013.01); C07C 7/144 (2013.01); B01D 2257/7025 (2013.01); B01D 2258/05 (2013.01)

(58) Field of Classification Search
  CPC ........ B01D 2256/245; B01D 2257/504; B01D 2257/7025; B01D 2258/05; B01D 53/22; B01D 53/30; C07C 7/144
  See application file for complete search history.

(56) References Cited

U.S. PATENT DOCUMENTS

2005/0000353 A1 1/2005 Nemser
2014/0251128 A1 9/2014 Graf
  (Continued)

FOREIGN PATENT DOCUMENTS

CN 111094725 A 5/2020
CN 111339205 A 6/2020
  (Continued)

OTHER PUBLICATIONS

European Search Report issued Mar. 4, 2024 in European Patent Application 21886149.0, 10 pages.
  (Continued)

*Primary Examiner* — Christopher P Jones
(74) *Attorney, Agent, or Firm* — Oblon, McClelland, Maier & Neustadt, L.L.P.

(57) ABSTRACT

A gas separation method including performing a gas separation operation that separates a source gas into a primary-side gas and a secondary-side gas with a membrane of a membrane module. The source gas contains a combustible component. The gas separation operation includes pressurizing the source gas and supplying the source gas to a primary side of the membrane module and depressurizing a secondary side of the membrane module to a pressure lower than an atmospheric pressure. The primary-side gas has a higher concentration of the combustible component than the secondary-side gas, and the gas separation method further includes detecting a composition of the secondary-side gas and stopping the gas separation operation in an instance in which the composition enters a specified range.

19 Claims, 1 Drawing Sheet

(51) Int. Cl.
   B01D 53/30          (2006.01)
   C07C 7/144          (2006.01)

(56)                     References Cited

U.S. PATENT DOCUMENTS

2017/0348643  A1    12/2017   Noguchi et al.
2019/0358591  A1    11/2019   Noguchi et al.
2020/0239797  A1     7/2020   Okada et al.

FOREIGN PATENT DOCUMENTS

EP          3 680 470  A1     7/2020
JP          3-131259   A      6/1991
JP          4-96995    A      3/1992
JP          5-293328   A     11/1993
JP          2007-260629 A    10/2007
JP          2009-24031  A     2/2009
JP          2009-242773 A    10/2009
JP          2016-93767  A     5/2016
JP          2016-155096 A     9/2016

JP          2018-153715 A    10/2018
WO          WO 2019/049629 A1  3/2019
WO          WO 2020/044992 A1  3/2020

OTHER PUBLICATIONS

Combined Chinese Office Action and Search Report issued Jun. 14, 2025 in Chinese Patent Application No. 202180072666.6 (with English Machine translation). 22 pgs.
International Search Report issued Dec. 7, 2021 in PCT/JP2021/039318 filed Oct. 25, 2021, (English Translation), 2 pages.
Japanese Office Action issued Apr. 22, 2025, in Japanese Application No. 2022-559127, (with unedited computer-generated English translation), 20 pages.
Chinese Office Action issued Sep. 20, 2025 in Chinese Patent Application No. 202180072666.6 (with unedited computer-generated English translation), 23 pages.
Japanese Office Action issued Sep. 24, 2025 in Japanese Patent Application No. 2022-559127 (with unedited computer-generated English translation), 12 pages.
Office Action issued Dec. 6, 2025, in corresponding Chinese Patent Application No. 202180072666.6, citing document 2, herein, 22 pages (with machine translation).
Zang Yu et al., The Science of Material on Gas Separation Membrane, Harbin Institute of Technology, Jan. 2017, 4 pages.

GAS SEPARATION METHOD AND GAS SEPARATION APPARATUS

CROSS REFERENCE TO RELATED APPLICATIONS

This application is a continuation of PCT/JP2021/039318, filed on Oct. 25, 2021, and claims priority to Japanese Patent Application No. 2020-181559, filed on Oct. 29, 2020. The entire contents of both are incorporated herein by reference.

TECHNICAL FIELD

The present invention relates to a method and an apparatus for separating combustible components from a gas that contains combustible components, by using a selective gas-permeable membrane (hereinafter also referred to as a "membrane").

BACKGROUND ART

Membrane separation is a commonly used technique for separating a gas that contains combustible components, such as methane, into combustible components and other gas components (e.g., Patent Literature 1 and 2).

Organic membranes, which have been frequently used for gas separation in the related art, have low separation performance (the "separation performance" refers to selectivity for combustible gases and non-combustible gases). Consequently, a permeate side has a high proportion of combustible gases. In instances where the concentration of combustible gases is high, if air from the outside is inadvertently introduced through a leak, the permeate side becomes within an explosive range easily.

Patent Literature 2 describes a method for separating a combustible organic vapor-containing exhaust gas with a membrane; in the method, to avoid an explosive range, an inert gas is passed on a permeate side through which a combustible organic vapor permeates.

CITATION LIST

Patent Literature

PTL 1: JP H4-96995 A
PTL 2: JP H5-293328 A

SUMMARY OF INVENTION

Technical Problem

In the instance of inorganic membranes, since they typically have high separation performance, a content of the substance that is selectively separated decreases in later stages of separation. As a result, a partial pressure that serves as a driving force for the separation decreases, which results in an extremely low amount of the gas that permeates. Accordingly, typically, it is necessary to increase the pressure of the non-permeate side or reduce the pressure of the permeate side, in order to increase the difference in the partial pressure between the permeate side and the non-permeate side of the membrane. In the instance where the pressure is increased, power used for a compressor or the like increases, which is economically disadvantageous. On the other hand, in the instance where the pressure of the permeate side is reduced, a small amount of air may be inadvertently introduced into the permeate gas through a leak. However, since the concentration of combustible components is very low, provided that the separation performance is high, the explosive range is typically not entered. The inventors focused their attention on the fact that the explosive range is entered only in instances in which, in the event of a leak, breakage of the membrane or the like additionally occurs, and, consequently an abrupt increase in the concentration of combustible components occurs. Accordingly, the invention of the present application was completed.

Specifically, an object of the present invention is to provide a gas separation method and a gas separation apparatus for performing, by using a membrane module, a membrane separation treatment on a gas that contains combustible components; the method and the apparatus are designed to immediately stop the operation of the membrane module in instances in which a combustible component is inadvertently introduced into the permeate gas.

Solution to Problem

A summary of the present invention is as follows.

[1] A gas separation method comprising a gas separation operation that separates a source gas into a primary-side gas and a secondary-side gas with a membrane of a membrane module, the source gas containing a combustible component, the gas separation operation including pressurizing the source gas and supplying the source gas to a primary side of the membrane module and depressurizing a secondary side of the membrane module to a pressure lower than an atmospheric pressure, the primary-side gas having a high concentration of the combustible component, the secondary-side gas having a low concentration of the combustible component, wherein the gas separation method includes detecting a composition of the secondary-side gas and stopping the gas separation operation in an instance in which the composition enters a specified range.

[2] A gas separation method comprising a gas separation operation that separates a source gas into a primary-side gas and a secondary-side gas with a membrane of a membrane module, the source gas containing a combustible component, the gas separation operation including pressurizing the source gas and supplying the source gas to a primary side of the membrane module and depressurizing a secondary side of the membrane module to a pressure lower than an atmospheric pressure, the primary-side gas having a high concentration of the combustible component, the secondary-side gas having a low concentration of the combustible component, wherein the gas separation method includes detecting a pressure or a flow rate of the secondary side and stopping the gas separation operation in an instance in which the detected pressure or flow rate exceeds a reference value.

[3] The gas separation method according to [2], wherein the reference value is a value 10 kPaG or more higher than a default value in an instance of the detected pressure, and the reference value is a value 50% or more higher than a default value in an instance of the flow rate.

[4] The gas separation method according to [1] and [2] or according to [1] and [3].

[5] The gas separation method according to [1] or [4], wherein, in the instance in which the composition enters the specified range, valves are closed, where one of the valves is disposed in a supply line for supplying the source gas to the membrane module, and another of the valves is disposed in a depressurization line of the membrane module.

[6] The gas separation method according to [1], [4], or [5], wherein the specified range is an explosive range.

[7] The gas separation method according to any one of [1] to [6], wherein the combustible component is methane.

[8] The gas separation method according to any one of [1] to [7], wherein a pressure of the secondary side is reduced to a pressure 30 kPa or more lower than the atmospheric pressure.

[9] The gas separation method according to any one of [1] to [8], wherein the membrane of the membrane module has a separation factor greater than or equal to 80.

[10] The gas separation method according to any one of [1] to [9], wherein, in an instance in which the source gas is inadvertently introduced, the composition enters the specified range.

[11] The gas separation method according to any one of [1] to [10], wherein the source gas is a biogas.

[12] A gas separation apparatus comprising a membrane separation device that comprises:

a membrane module that separates a source gas into a primary-side gas and a secondary-side gas with a membrane of the membrane module, the source gas containing a combustible component, the primary-side gas having a high concentration of the combustible component, the secondary-side gas having a low concentration of the combustible component;

a supply line including a pressure pump that pressurizes the source gas and supplies the source gas to a primary side of the membrane module; and a permeate line including a vacuum pump that depressurizes a secondary side of the membrane module, wherein;

the membrane separation device includes a detector that detects a composition of the secondary-side gas, and a controller that stops the pressure pump and the vacuum pump in an instance in which the composition reaches a specified range.

[13] A gas separation apparatus comprising a membrane separation device that comprises:

a membrane module that separates a source gas into a primary-side gas and a secondary-side gas with a membrane of the membrane module, the source gas containing a combustible component, the primary-side gas having a high concentration of the combustible component, the secondary-side gas having a low concentration of the combustible component;

a supply line including a pressure pump that pressurizes the source gas and supplies the source gas to a primary side of the membrane module; and a permeate line including a vacuum pump that depressurizes a secondary side of the membrane module, wherein;

the membrane separation device includes a detector that detects a pressure or a flow rate of the secondary side, and a controller that stops the pressure pump and the vacuum pump in an instance in which the pressure or the flow rate of the secondary side becomes greater than a specified value.

[14] The gas separation apparatus according to [13], wherein the reference value is a value 10 kPaG or more higher than a default value in an instance of the detected pressure, and the reference value is a value 50% or more higher than a default value in an instance of the flow rate.

[15] The gas separation apparatus according to [12] and [13] or according to [12] and [14].

[16] The gas separation apparatus according to [12] or [15], wherein a valve controller is included, which is a valve controller that causes valves to be closed in the instance in which the composition reaches the specified range, where one of the valves is disposed in a supply line for supplying the source gas to the membrane module, and another of the valves is disposed in a depressurization line of the membrane module.

[17] The gas separation apparatus according to [12], [15], or [16], wherein the specified range is an explosive range.

[18] The gas separation apparatus according to any one of [12] to [17], wherein the combustible component is methane.

[19] The gas separation apparatus according to any one of [12] to [18], wherein the vacuum pump is a vacuum pump that reduces a pressure of the secondary side to less than or equal to −30 kPaG.

[20] The gas separation apparatus according to any one of [12] to [19], wherein the membrane of the membrane module has a separation factor greater than or equal to 80.

[21] The gas separation apparatus according to any one of [12] to [20], wherein, in an instance in which the source gas is inadvertently introduced, the composition enters the specified range.

[22] The gas separation apparatus according to any one of [12] to [21], wherein the source gas is a biogas. Advantageous Effects of Invention The gas separation method and the gas separation apparatus of the present invention enable the operation of a membrane module to be immediately stopped in instances in which a combustible component is inadvertently introduced into the permeate gas.

DESCRIPTION OF EMBODIMENTS

Figure 1:
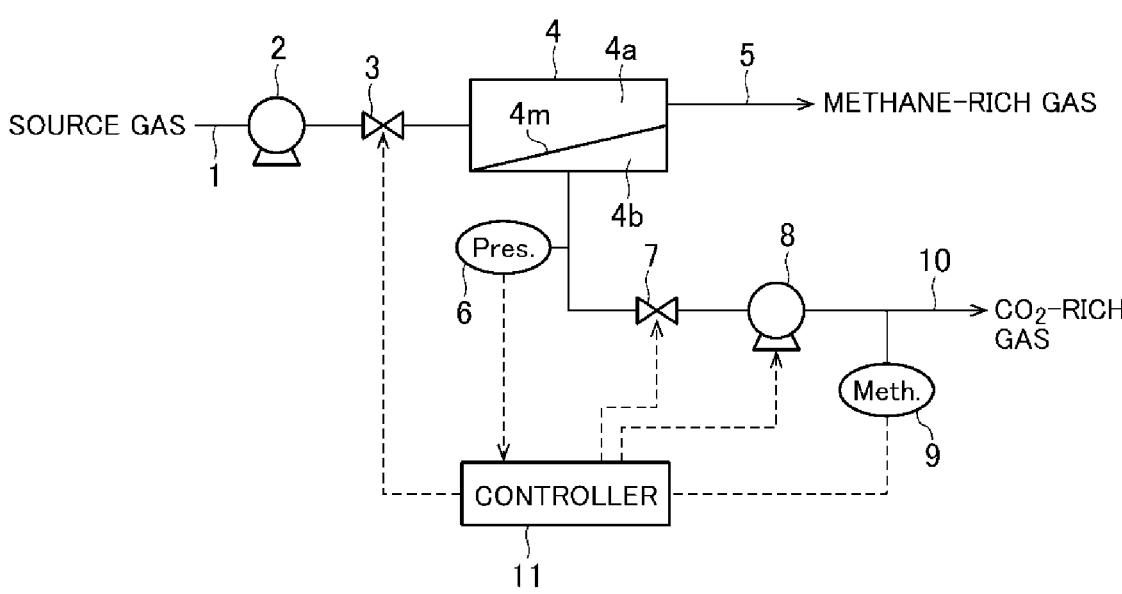
FIG. 1 is a diagram illustrating a configuration of a gas separation apparatus.

The present invention will be described in detail below.

In the present invention, the treatment target gas (source gas) contains one or more combustible components and one or more non-combustible components. Examples of the combustible components include, but are not limited to, hydrocarbon gases, such as methane, ethane, and propane, hydrogen, and ammonia. Examples of the non-combustible components include, but are not limited to, carbon dioxide gas ($CO_2$), nitrogen, and halogen gas.

Examples of the source gas containing such combustible components and non-combustible components include, but are not limited to, biogases, landfill gases, hot spring gases, coal mine gases, and natural gases. Note that the biogas is a gas produced by methane fermentation of biomass and may be subclassified as follows: a biogas produced from landfill-derived biomass may be referred to as a "landfill gas", a biogas produced from sewage sludge-derived biomass as a "digester gas", and a biogas produced from food waste- or livestock waste-derived biomass as a "biogas".

The concentration of combustible components in the source gas is, approximately, 30 to 70% (vol. %, the same applies hereinafter) for biogases, 20 to 70% for landfill gases, depending on how the gases were collected, and 10 to 90% in terms of methane for hot spring gases, where the composition is one in which the concentration of saturated water vapor is not taken into account.

From the standpoint of cost effectiveness and avoidance of explosion, it is preferable that the concentration of combustible components in the source gas be 20 to 95%.

Preferred examples of a membrane module include a membrane module that includes a large number of tubular separation membranes disposed in a vessel and in which a source gas can be passed through an outer side of the tubular separation membranes, and non-combustible components can be allowed to permeate into an inner side of the tubular separation membranes or in which a source gas can be passed through the inner side of the tubular separation membranes, and non-combustible components can be allowed to permeate to the outer side of the tubular separation membranes. These are not intended to be limiting and can be applied to a honeycomb structure, a hollow fiber structure, a sheet structure, and the like.

Preferably, the tubular separation membranes are those that include a molecular sieve membrane, which serves as a selective gas-permeable membrane, disposed on an inner peripheral surface and/or an outer peripheral surface of tubular porous substrates.

Porous Substrate

The porous substrate serves as a support for supporting the molecular sieve membrane. The material that forms the porous substrate is not particularly limited, and any of a variety of materials, such as glass, ceramics, metals, formed carbon materials, and resins, can be employed. In the instance of ceramic supports, any ceramic may be used as long as the ceramic is a chemically stable porous inorganic material that enables the formation of a crystallized zeolite in the form of a membrane, on a surface or the like of the material. Specifically, the ceramic may be, for example, a ceramic sintered body made of, for instance, silica, α-alumina, γ-alumina, mullite, zirconia, titania, yttria, silicon nitride, silicon carbide, or the like. Among these, aluminas, such as α-alumina and γ-alumina, and mullite are preferable, and aluminas are particularly preferable. In instances where any of these supports is used, the support can be easily partially transformed into a zeolite, and, consequently, strong bonding between the support and the zeolite is achieved, which facilitates the formation of a membrane that is dense and has a high separation performance.

In the present invention, the porous substrate itself need not have the functions of a molecular sieve. The porous substrate has small pores (voids, vacancies) interconnecting an outer wall side (outer peripheral surface) and an inner wall side (inner peripheral surface).

The porous substrate has a porosity that is typically greater than or equal to 20%, preferably greater than or equal to 25%, and more preferably greater than or equal to 30% and is typically less than or equal to 80%, preferably less than or equal to 60%, and more preferably less than or equal to 50%. An average pore diameter of the porous substrate is typically greater than or equal to 0.01 μm, preferably greater than or equal to 0.05 μm, and more preferably greater than or equal to 0.1 μm, and the upper limit thereof is typically less than or equal to 20 μm, preferably less than or equal to 10 μm, and more preferably less than or equal to 5 μm. When the porous substrate has such pores, the porous substrate has sufficient strength and, therefore, can appropriately support the molecular sieve membrane; in addition, the porous substrate can allow permeation therethrough, at a sufficient speed, of the molecules that have permeated through the molecular sieve membrane, and the porous substrate can also allow molecules to reach the molecular sieve membrane at a sufficient speed. Note that the porosity and the pore diameter of the porous substrate can be easily determined, for instance, by mercury intrusion porosimetry or by SEM examination of a cross section. The average pore diameter can be determined in a similar manner. Alternatively, the average pore diameter can be calculated from a volume and a mass, based on a true specific gravity.

In instances where a zeolite membrane that serves as the molecular sieve membrane is formed, the porous substrate is one in which the openings of the pores extending from the outer peripheral surface to the inner peripheral surface have a maximum diameter that is typically less than or equal to 10 μm and preferably less than or equal to 8 μm. Preferably, the lower limit of the maximum diameter is greater than or equal to 0.05 μm. Furthermore, the portions extending from the outer peripheral surface to the inner peripheral surface may have a pore diameter that is entirely uniform or have a pore diameter that varies locally or progressively, as described in JP 2005-270887 A, for example.

In the tubular porous substrates, it is preferable that cross sections perpendicular to a tube axis direction associated with the outer peripheral surface and the inner peripheral surface be both circular. A thickness (difference between a radius of the outer peripheral surface and a radius of the inner peripheral surface) of the tubular porous substrate is not particularly limited. For example, the thickness is preferably greater than or equal to 0.5 mm, more preferably greater than or equal to 0.8 mm, and even more preferably greater than or equal to 1.0 mm, depending on the material, the porosity, and the like.

An inner diameter of the tubular porous substrate is not particularly limited. For example, a ratio of the inner diameter (diameter) to the above-mentioned thickness of the porous substrate (inner diameter (mm)/thickness (mm)) is preferably less than or equal to 20, more preferably less than or equal to 17, even more preferably less than or equal to 13, and particularly preferably less than or equal to 9, depending on the material, the porosity, and the like. In instances where the porous substrate is made of a ceramic sintered body, it is preferable that the inner diameter be greater than or equal to 3 mm, particularly, greater than or equal to 5 mm, and less than or equal to 20 mm, particularly, less than or equal to 15 mm.

A length (axial length) of the porous substrate is not particularly limited.

Molecular Sieve Membrane

The molecular sieve membrane is formed on the outer peripheral surface and/or the inner peripheral surface of the porous substrate. The molecular sieve membrane may have any form as long as the molecular sieve membrane can appropriately perform the functions of the molecular sieve.

The molecular sieve membrane may either be an organic membrane or an inorganic membrane. Preferably, the molecular sieve membrane is an inorganic membrane. Preferably, the inorganic membrane is a zeolite membrane, a silica membrane, a carbon membrane, or a combination thereof. Among these, a zeolite membrane or a silica membrane is preferable. In particular, a zeolite membrane is preferable from the standpoint of separation performance, water resistance, and durability.

In the instance where a zeolite membrane is used as the molecular sieve membrane, it is preferable that the zeolite be an aluminosilicate; alternatively, it is also possible that a metal element, such as Ga, Fe, B, Ti, Zr, Sn, or Zn, be used instead of Al, or an element, such as Ga, Fe, B, Ti, Zr, Sn, Zn, or P, be included together with Al, provided that the performance of the membrane is not significantly impaired.

Preferably, the framework of the crystalline zeolite that forms the pores of the zeolite membrane is an 8- or less-membered oxygen ring. More preferably, the framework is a 6- to 8-membered oxygen ring.

Examples of the structure of the zeolite include AEI, AFG, ANA, CHA, DDR, EAB, ERI, ESV, FAR, FRA, GIS, ITE, KFI, LEV, LIO, LOS, LTA, LTN, MAR, MWF, PAU, RHO, RTH, SOD, STI, TOL, and UFI. In particular, it is preferable to use a membrane formed of a zeolite of a type of AEI, CHA, DDR, ERI, KFI, LEV, MWF, PAU, RHO, RTH, SOD, LTA, or UFI, and it is more preferable to use a membrane formed of a zeolite of a type of CHA, DDR, MWF, RHO, or SOD. Regarding zeolites having an n-membered oxygen ring, the value of n represents the number of oxygen atoms that is highest among those of the pores formed by the zeolite framework and T elements (elements other than oxygen that form the framework).

In the instance where a zeolite membrane that serves as the molecular sieve membrane is synthesized, an organic template (structure-directing agent) may be used if necessary. Typically, the template is not particularly limited as long as the template enables the formation of the desired zeolite structure, and, if the synthesis can be achieved without any template, there is no need to use a template.

In the instance where a silica membrane is used as the molecular sieve membrane, a content of silica in the silica membrane is not particularly limited as long as the effects of the present invention are not significantly impaired. For example, a proportion of silicon to all electropositive elements including silicon is typically greater than or equal to 50 mol %, in a silicon oxide composition.

The silica membrane is formed on an inorganic porous substrate with a sol-gel process, a CVD process, a polymer precursor process, or the like. In the sol-gel process, the silica membrane can be formed by reacting a metal alkoxide with water on an inorganic porous substrate to cause hydrolysis and dehydration condensation, thereby forming a gel. Furthermore, in a counter diffusion CVD process, the silica membrane can be formed, for example, as follows: in instances where the inorganic porous substrate is a porous tubular substrate, oxygen is passed through the inner side, and a silica source through the outer side, to deposit an amorphous silica layer within the pores of the substrate. Furthermore, in the polymer precursor process, the silica membrane can be formed by applying a silica precursor, such as an alkoxysilane or a polysilazane, to an inorganic porous substrate and subsequently performing a heat treatment thereon.

In the instance where a carbon membrane is used as the molecular sieve membrane, the carbon membrane is formed by dip coating (immersion-coating) a carbon membrane precursor solution onto a porous substrate, performing a heat treatment thereon at a temperature of approximately 600 to 800° C., and drying the resultant. Examples of the carbon membrane precursor include aromatic polyimides, polypyrrolones, polyfurfuryl alcohols, polyvinylidene chlorides, phenolic resins, lignin derivatives, wood tars, and bamboo tars. A preferred solvent that may be used is an organic solvent, such as tetrahydrofuran, acetone, methanol, ethanol, or N-methylpyrrolidone.

A thickness of the molecular sieve membrane is not particularly limited. Regarding zeolite membranes, the lower limit of the thickness is typically greater than or equal to 0.01 µm. The upper limit of the thickness is preferably less than or equal to 30 µm and more preferably less than or equal to 10 µm. Regarding silica membranes, the membranes may be formed of a single layer or two or more layers, and the thickness of the membranes is preferably greater than or equal to 1 nm. The thickness is preferably less than or equal to 10 µm and more preferably less than or equal to 1 µm. Regarding carbon membranes, the thickness thereof is preferably greater than or equal to 0.05 µm and more preferably greater than or equal to 0.1 µm. The upper limit of the thickness is preferably less than or equal to 5 mm and more preferably less than or equal to 500 µm. It is preferable that the thickness of the membrane be small, provided that the performance of the membrane is not significantly impaired.

Methods for forming the molecular sieve membrane on a surface of the porous substrate are not limited to the methods described above. Examples of the methods include (1) a method in which a material that can form a molecular sieve membrane is firmly attached to a surface of a porous substrate with a binder or the like; (2) a method in which a porous substrate is impregnated with a slurry or a solution in which a material that can form a molecular sieve membrane is dispersed or dissolved, to cause the material to be firmly attached to a surface of the porous substrate; and (3) a method in which a material (in particular, for a zeolite) that can form a molecular sieve membrane is crystallized in the form of a membrane on a surface of a porous substrate (see, for example, the pamphlet of WO 2013/125660 A1, and the like).

The molecular sieve membrane may be formed only on the outer peripheral surface of the porous substrate; the molecular sieve membrane may be formed only on the inner peripheral surface of the porous substrate; or the molecular sieve membrane may be formed on both the outer peripheral surface and the inner peripheral surface of the porous substrate. Any of these forms may be employed. Typically, from the standpoint of an internal contraction force possessed by the coated member, it is desirable that the molecular sieve membrane be formed on the outer peripheral surface of the porous substrate.

A separation factor α of the membrane is greater than or equal to 80, preferably greater than or equal to 100, and particularly preferably greater than or equal to 150.

The separation factor α is defined by the following equation.

[Math. 1]

$$\text{Separation factor } a = \frac{Y_{CO2}/Y_{CH4}}{X_{CO2}/X_{CH4}} \tag{1}$$

$Y$: Composition of gas of secondary side $X$: Composition of gas of primary side The separation factor α may vary depending on separation conditions. Here, the separation factor α is defined as each of the values obtained under the separation conditions of the separation operations performed by the respective membrane modules.

In an aspect of the present invention, a secondary side (permeate side) of the membrane module is depressurized with a vacuum pump so that the pressure can become lower than the atmospheric pressure. Furthermore, a composition, a pressure, a flow rate, and the like of the gas of the secondary side are analyzed by performing detection on-line or in-line, and the supply of the source gas and the vacuum pump are stopped in the following instances: instances in which the composition of the gas of the secondary side enters a specified range (e.g., a range of the concentration of combustible components of greater than 20 vol. % or an explosive range) as a result of, for instance, damage, such as breakage, in the membrane; instances in which the concentration of oxygen of the secondary side enters a specified range (e.g., a range of greater than 1 vol. % or an explosive range); and/or instances in which at least one of the pressure and the flow rate, of the gas of the secondary side, exceeds a reference value. Additionally, valves installed on a source gas entry side and a permeate gas exit side of the membrane module may be closed.

The specified range can be entered for various reasons. The most likely reason is believed to be inadvertent introduction of the source gas. Inadvertent introduction of the source gas can occur in instances in which the separation membrane is broken during the separation operation or in instances in which a seal of the separation membrane becomes insufficient.

The reference value of the pressure of the gas of the secondary side is, for example, a value 10 kPa higher than a default value or a value of a degree of depressurization specified for a secondary side 4b. Furthermore, the reference value of the flow rate of the gas of the secondary side is, for example, a value 50% higher than a default value.

As used herein, the expression "pumps are stopped" means that the supply of the source gas and depressurization are stopped; this encompasses cases in which a state, such as an idling state, is created in which the supply of a material, pressurization, and depressurization by the pumps are not performed.

FIG. 1 illustrates an example of a gas separation apparatus equipped with a membrane module.

The source gas containing combustible components is introduced into a primary side 4a of a membrane module 4 through a tube 1, which includes a pressure pump 2 and a valve (emergency shut-off valve) 3. A membrane 4m divides the interior of the membrane module 4 into the primary side 4a and the secondary side 4b.

In this embodiment, the source gas contains methane ($CH_4$), which is a combustible component, and carbon dioxide gas ($CO_2$), which is a non-combustible component, and the membrane 4m is a zeolite membrane. Carbon dioxide gas can permeate through the zeolite membrane 4m, and methane cannot substantially permeate through the zeolite membrane 4m. Accordingly, a primary side exit gas, which is methane-rich, flows out to a tube 5 from a primary side outlet of the membrane module 4.

A tube 10 is connected to the secondary side 4b of the membrane module 4. The tube 10 includes a pressure sensor 6, a valve (emergency shut-off valve) 7, a vacuum pump 8, and a methane sensor 9 for detecting a concentration of methane. By virtue of the vacuum pump 8, the secondary side 4b has a reduced pressure less than or equal to a specified degree of depressurization. The reduced pressure is preferably less than or equal to −30 kPaG and particularly preferably less than or equal to −50 kPaG. The sensor is not limited to methane sensors, and any means capable of detecting the composition may be used. A gas sensor operable in a known manner may be used. The use of a methane sensor is preferable from the standpoint of detecting the combustible gas.

Carbon dioxide gas permeates through the zeolite membrane 4m and is drawn as a $CO_2$ rich gas through the tube 10.

A controller 11 is configured to include detection signals input from the pressure sensor 6 and the methane sensor 9. The controller 11 is configured to stop the pumps 2 and 8 and close the valves 3 and 7 in an emergency. The stopping operation for emergencies is not limited to the stopping of the pumps, and any other operation that stops the separation operation may be employed.

Now, an example of steady-state operating conditions (e.g., material balance) for the membrane separation device illustrated in FIG. 1 will be described.

An amount of supply of the source gas per unit time is such that $CO_2$ is in an amount of 40 molar parts, and $CH_4$ is in an amount of 60 molar parts. The source gas is pressurized to 600 kPaG with the pressure pump 2 and supplied to the membrane module 4. An amount of exit of the methane-rich gas, which is the primary side exit gas, per unit time is such that $CO_2$ is in an amount of 3 molar parts, and $CH_4$ is in an amount of 58 molar parts, provided that an absolute pressure of the permeate side of the membrane is reduced to −30 kPaG, a permeance for $CO_2$ is 2.0E-06 mol/m²/Pa/s, an area of the membrane is 2.6 m², and the separation factor α of the membrane is 83.

An amount of exit of the $CO_2$-rich gas, which is the secondary side exit gas, per unit time is such that $CO_2$ is in an amount of 37 molar parts, and $CH_4$ is in an amount of 2 molar parts.

In general, zeolite separation membranes have high separation performance, and, therefore, if a supply pressure of the source gas is low, the partial pressure of the separation target substance, which acts as a driving force for the separation, decreases at or near the exit side of the primary chamber 4a, and as a result, the separation performance is reduced. Accordingly, this embodiment uses the vacuum pump 8.

In the instance of the configuration that depressurizes the secondary side 4b, if air is leaked into the secondary side 4b through a leak, methane may flow into the secondary side 4b in the event that, for instance, damage, such as breakage, occurs in the separation membrane; consequently, the composition of the gas of the secondary side 4b may enter the explosive range.

Accordingly, in this embodiment, the flow of methane into the secondary side 4b is detected with the methane sensor 9, and if the concentration of methane enters a specified range (e.g., a range of the concentration of methane of greater than 20 vol. % or the explosive range), a determination is made that an anomaly, such as breakage of the membrane, has occurred, and the pressure pump 2 and the vacuum pump 8 are stopped. Additionally, the valves 3 and 7 may be closed. Note that the pressure sensor 6 and/or a flowmeter are installed on the tube 10; in instances where the pressure exceeds a reference value (e.g., a value 10 kPa higher than a default value or a value of the degree of depressurization specified for the secondary side 4b) and/or in instances where the detected flow rate exceeds a reference value (e.g., a value 50% higher than a default value), the pumps 2 and 8 may be stopped to stop the separation operation. Additionally, the valves 3 and 7 may be closed. The reference values may be preset in accordance with the separation conditions for the separation target gas.

The pressure pump 2 and the vacuum pump 8 may be stopped in instances where the concentration of methane in the gas of the secondary side 4b enters a specified range (e.g., a range of the concentration of methane of greater than 20 vol. % or the explosive range), plus in instances where the pressure exceeds a reference value (e.g., a value 10 kPa higher than a default value or a value of the degree of depressurization specified for the secondary side 4b) and/or in instances where the detected flow rate exceeds a reference value (e.g., a value 50% higher than a default value). Additionally, the valves 3 and 7 may be closed.

Procedure for Restarting Apparatus After Stopping of Apparatus

In the instance where the apparatus is stopped, the restart is carried out with the procedure described below in (1) to (7).

(1) Discharge Gas

For the primary side, the valve 3 and the valve 7 are closed, and subsequently, the residual gas is discharged from the tube 5 to return the pressure of the interior of the module to a normal pressure.

For the secondary side, the pressure recovery may be carried out with the gas that has permeated through the membrane, or the pressure recovery may be carried out with air from a separately provided line.

Subsequently, an inert gas, such as nitrogen, and air are introduced from the tube 1 to replace the gas within the module. In this instance, the vacuum pump 8 may be activated.

(2) Open Module (3) Identify Damaged Separation Membranes

For example, a method described in JP 2020-192482 A (a method that uses a pitot tube for the identification) may be employed.

(4) Replace Damaged Separation Membranes (5) Close Module (6) Perform Preliminary Operation The vacuum pump 8 is activated, and subsequently, a source gas is introduced through the tube 1. After a permeation amount or the composition of the secondary side is stabilized, the separation operation is resumed.

(7) Resume Separation

Figure 2:
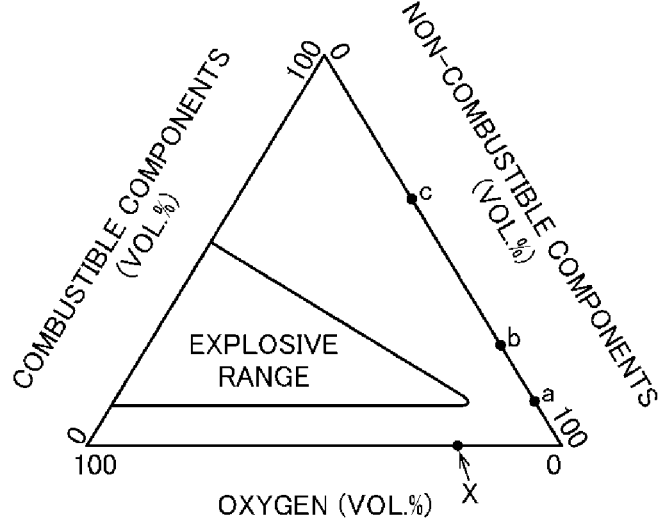
FIG. 2 is a ternary diagram illustrating a composition of a gas.

In general, regarding the ternary system of methane ($CH_4$), carbon dioxide gas ($CO_2$), and oxygen ($O_2$), the gas that has permeated through a zeolite membrane contains substantially no $CH_4$, provided that the separation performance of the separation membrane is high. Accordingly, even if air is inadvertently introduced into the permeate gas through a leak during the depressurization, the composition does not enter the explosive range, with the composition changing from a point a to a point X as illustrated in FIG. 2. Likewise, in instances where the $CH_4$ concentration is approximately less than or equal to 20%, even if air is inadvertently introduced into the permeate gas through a leak during the depressurization, the composition substantially does not enter the explosive range, with the composition changing from a point b to the point X. However, if breakage, abrasion, and/or the like of the membrane occurs in addition to the leak during the depressurization, and, consequently, methane derived from the source gas and oxygen are inadvertently introduced into the permeate gas, the composition may enter the explosive range, with the composition changing from a point c to the point X. Accordingly, in instances where the source gas contains methane and carbon dioxide as major components, the above-described embodiment produces a large effect in the manner in which the flow of methane into the secondary side 4b is detected with a methane sensor or with a pressure sensor and/or a flowmeter, and in instances where the concentration of methane enters a reference range, or the pressure or the flow rate exceeds a reference value, the pressure pump 2 and the vacuum pump 8 are stopped. Additionally, the configuration may include the closing of the valves 3 and 7. In this case, the effect is increased.

In the present embodiment, the module is provided as a single module. Alternatively, the module may be a plurality of the modules that are connected to one another via a serial connection, a parallel connection, or a combination of serial and parallel connections. In instances where the module is a plurality of the modules that are connected to one another, the detection of the composition, the flow rate, or the pressure may be performed for each of the modules, or the detection of the composition, the flow rate, or the pressure may be performed collectively for a particular number of the modules.

Although the present invention has been described in detail using specific embodiments, it will be apparent to those skilled in the art that various modifications can be made without departing from the spirit and scope of the present invention.

This application is based on Japanese Patent Application No. 2020-181559 filed on Oct. 29, 2020, which is incorporated by reference in its entirety.

REFERENCE SIGNS LIST

2 PRESSURE PUMP
3, 7 VALVE
4 MEMBRANE MODULE
6 PRESSURE SENSOR
9 METHANE SENSOR

The invention claimed is:

1. A gas separation apparatus comprising a membrane separation device that comprises:

a membrane module that separates a source gas into a primary-side gas and a secondary-side gas with a membrane of the membrane module, wherein the source gas contains a combustible component, wherein the primary-side gas has a higher concentration of the combustible component than the secondary-side gas;

a supply line including a pressure pump that pressurizes the source gas and supplies the source gas to a primary side of the membrane module; and a permeate line including a vacuum pump that depressurizes a secondary side of the membrane module, wherein the membrane separation device includes:

a detector that detects a composition of the secondary-side gas, and a controller that stops the pressure pump and the vacuum pump in an instance in which the composition reaches a specified range, wherein the membrane of the membrane module has a separation factor greater than or equal to 80.

2. A gas separation apparatus comprising a membrane separation device that comprises:

a membrane module that separates a source gas into a primary-side gas and a secondary-side gas with a membrane of the membrane module, wherein the source gas contains a combustible component, wherein the primary-side gas has a higher concentration of the combustible component than the secondary-side gas;

a supply line including a pressure pump that pressurizes the source gas and supplies the source gas to a primary side of the membrane module; and a permeate line including a vacuum pump that depressurizes a secondary side of the membrane module, wherein the membrane separation device includes:

a detector that detects a pressure or a flow rate of the secondary side, and a controller that stops the pressure pump and the vacuum pump in an instance in which the pressure or the flow rate of the secondary side becomes greater than a reference value, wherein the membrane of the membrane module has a separation factor greater than or equal to 80.

3. The gas separation apparatus according to claim 2, wherein the reference value is a value at least 10 kPaG higher than a default value in an instance of the pressure, and wherein the reference value is a value at least 50% higher than a default value in an instance of the flow rate.

4. The gas separation apparatus according to claim 1, further comprising a valve controller, wherein the valve controller causes valves to be closed in the instance in which the composition reaches the specified range, where one of the valves is disposed in a supply line for supplying the source gas to the membrane module, and another of the valves is disposed in a depressurization line of the membrane module.

5. The gas separation apparatus according to claim 1, wherein the specified range is an explosive range.

6. The gas separation apparatus according to claim 1, wherein the combustible component is methane, and the source gas further comprises carbon dioxide.

7. The gas separation apparatus according to claim 1, wherein the vacuum pump is a vacuum pump that reduces a pressure of the secondary side to less than or equal to −30 kPaG.

8. The gas separation apparatus according to claim 1, wherein, in an instance in which the source gas is inadvertently introduced, the composition enters the specified range.

9. The gas separation apparatus according to claim 1, wherein the source gas is a biogas.

10. The gas separation apparatus according to claim 2, wherein the combustible component is methane, and the source gas further comprises carbon dioxide.

11. A gas separation method, comprising:

performing a gas separation operation with the gas separation apparatus of claim 1 that separates the source gas into the primary-side gas and the secondary-side gas with the membrane of the membrane module, wherein the source gas contains a combustible component, the gas separation operation including:

pressurizing the source gas and supplying the source gas to the primary side of the membrane module, and depressurizing the secondary side of the membrane module to a pressure lower than an atmospheric pressure;

wherein the primary-side gas has a higher concentration of the combustible component than the secondary-side gas, and wherein the gas separation method further includes detecting the composition of the secondary-side gas; and stopping the gas separation operation in an instance in which the composition enters the specified range.

12. A gas separation method, comprising:

performing a gas separation operation with the gas separation apparatus of claim 2 that separates the source gas into the primary-side gas and the secondary-side gas with the membrane of the membrane module, wherein the source gas contains a combustible component, the gas separation operation including:

pressurizing the source gas and supplying the source gas to the primary side of the membrane module, and depressurizing the secondary side of the membrane module to a pressure lower than an atmospheric pressure;

wherein the primary-side gas has a higher concentration of the combustible component than the secondary-side gas, and wherein the gas separation method further includes detecting the pressure or the flow rate of the secondary side; and stopping the gas separation operation in an instance in which a detected pressure or the pressure or the flow rate exceeds the reference value.

13. The gas separation method according to claim 12, wherein the reference value is a value at least 10 kPaG higher than a default value in an instance of the detected pressure, and wherein the reference value is a value at least 50% higher than a default value in an instance of the flow rate.

14. The gas separation method according to claim 11, wherein, in the instance in which the composition enters the specified range, valves are closed, where one of the valves is disposed in the supply line for supplying the source gas to the membrane module, and another of the valves is disposed in a depressurization line of the membrane module.

15. The gas separation method according to claim 11, wherein the specified range is an explosive range.

16. The gas separation method according to claim 11, wherein the combustible component is methane.

17. The gas separation method according to claim 11, wherein the pressure of the secondary side is reduced to a pressure 30 kPa or more lower than the atmospheric pressure.

18. The gas separation method according to claim 11, wherein, in an instance in which the source gas is inadvertently introduced, the composition enters the specified range.

19. The gas separation method according to claim 11, wherein the source gas is a biogas.

* * * * *